United States Patent [19]

Elsdon et al.

[11] 4,255,598
[45] Mar. 10, 1981

[54] SUPPRESSION OF ALDEHYDE FORMATION IN XYLENE

[75] Inventors: Ronald Elsdon, St. Charles; Dennis L. Stauffenberg, Mahattan, both of Ill.

[73] Assignee: Standard Oil Company (Indiana), Chicago, Ill.

[21] Appl. No.: 106,698

[22] Filed: Dec. 26, 1979

[51] Int. Cl.³ .............................................. B01D 3/34
[52] U.S. Cl. .......................................... 585/3; 203/6; 203/60; 208/48 AA
[58] Field of Search ........................................ 585/2–3; 208/48 AA; 203/6, 60–61

[56] References Cited

U.S. PATENT DOCUMENTS 2,813,912  11/1957  Gwynn et al. ........................ 203/6 X

*Primary Examiner*—Herbert Levine
*Assistant Examiner*—G. E. Schmitkons
*Attorney, Agent, or Firm*—Fred R. Ahlers; William T. McClain; William H. Magidson

[57] ABSTRACT

Xylenes can by merely being contacted with air over a period of time or during storage at temperatures upward from 60° C. develop from 55 to 60 ppm of tolualdehyde. Such tolualdehyde formation can be suppressed by dissolving in the xylene a small amount of thiodipropionic acid or a di(alkyl)ester thereof.

4 Claims, No Drawings

SUPPRESSION OF ALDEHYDE FORMATION IN XYLENE

FIELD OF THE INVENTION

This invention relates to the suppression of the formation of tolualdehyde in xylene contacted with air at temperatures upward from 50° C. and more specifically pertains to such suppression of tolualdehyde formation in xylene contacted with air at a temperature of from 50° C. up to its normal boiling point (138.5° to 144° C. at 760 mm Hg) by dissolving in the xylene a small amount of thiodipropionic acid or one of its dialkyl esters soluble in the xylene.

STATE OF THE ART

Little or no concern has been expressed in the art pertaining to the use of xylenes with respect to the formation of tolualdehyde in small or even large amounts as an impurity which might convey undesirable properties or conditions to other materials, for example, to dimethyl terephthalate or maleic anhydride, or phthalic anhydride, with which such aldehyde contaminated xylene may contact. Xylenes have been proposed as solvents for the purification of dimethyl terephthalate (DMT) by extraction and/or recrystallization and any xylene remaining in the DMT is removed as a forecut of reduced pressure fractionation.

Recently, concern has arisen for the deliberate formation of tolualdehyde because its further oxidation under liquid phase conditions to a phthalic acid apparently avoids co-production of one or more undesirable and difficultly removable impurities.

In any event the state of the art is rather silent with respect to the formation of small amounts, for example 70 to 150 ppm, o-tolualdehyde in o-xylene upon casual contact with air even at moderate temperature conditions; e.g. at a temperature upward from 50° C.

We have discovered that o-xylene at a temperature of 60° C. can by merely being contacted with air in storage develop 55 to 60 weight parts o-tolualdehyde per million weight parts of o-xylene in 72 hours and develop 20 to 25 additional weight parts o-tolualdehyde per million weight parts of o-xylene at 60° C. in 45 hours when air is injected into the liquid o-xylene. We have also discovered that the rate of formation of p- or m-tolualdehyde in p-xylene or m-xylene is faster than the rate of formation of o-tolualdehyde in o-xylene. For example, at 60° C. quiescent p-xylene in contact with air will in 72 hours have a 111 ppm increase in p-tolualdehyde content.

In addition to the use of a xylene as solvent for purification or partial purification of dimethyl terephthalate by recrystallization, other uses for xylenes have been proposed. For example, xylenes have been proposed for use in the removal of water by azeotropic distillation of aqueous acetic acid containing 6 to 15 weight percent water. Also, xylene has been proposed for use in the recovery of maleic anhydride or phthalic anhydride from an aqueous solution of maleic acid or o-phthalic acid by forming a water-xylene azeotrope for distillative removal of solvent water and water split out by the formation of the anhydride. In those uses of a xylene its tolualdehyde can contaminate and discolor the diester or the anhydride product.

Treatment of the xylene containing tolualdehyde with a solid absorbent such as a molecular sieve having pore sizes upward from about 9 Å diameter can remove the tolualdehyde. However, the absorbent would, when used commercially in a bed of one meter in diameter and 10 meters long, have to be regenerated every 8 to 10 hours. But such removal of tolualdehyde would not prevent the tolualdehyde from forming again when the solid absorbent treated xylene was exposed to air.

However, we have discovered a relatively simple means for treating a xylene which is or may be contacted with air in its use so that the tolualdehyde does not form and hence need not be removed so the tolualdehyde does not contaminate the compound it is being used with to purify or form.

STATEMENT OF THE INVENTION

The formation of a tolualdehyde in a xylene can be suppressed by dissolving in the xylene a small amount of thiodipropionic acid or a dialkyl ester thereof. The "small amount" of thiodipropionic acid or its xylene soluble diester is upward from 100 weight parts of the dibasic acid per million weight parts of xylene or the chemical equivalent thereof as the diester.

The diester can be any one from dimethyl up to the dialkyl ester formed from the highest carbon content alkanol currently available which diester is soluble in a xylene. Preferably, the diester is a di($C_6$ to $C_{18}$ alkyl)ester of thiodipropionic acid for the suppression of tolualdehyde formation in a xylene.

The minimum use of thiodipropionic acid is 100 ppm based on the xylene. The upper limit, as a practical economic matter, is 400 ppm based on the weight of xylene but larger amounts can be used where process economics are of no concern. The use of such larger amounts, e.g., above 400 ppm based on the weight of the xylene will not have any disadvantageous technical effects.

The chemically equivalent amounts of the dialkyl esters of thiodipropionic acid useful according to this invention can be readily ascertained by dividing the molecular weight of the diester by the molecular weight of thiodipropionic acid and multiplying the resulting quotient by the foregoing 100 to 400 ppm range for the free dibasic acid. For example, said quotient for dilauryl thiodipropionate (a di-$C_{16}$ alkyl ester) is 3.5. Thus the range for using the dilauryl ester is from 350 up to 1400 ppm based on the xylene.

The following examples will illustrate the ease of tolualdehyde formation in a xylene and how the present inventive concept suppresses the tolualdehyde formation.

Firstly, in the following three comparative examples fresh xylene is heated to 60° C. either in contact with air or with air injected into the heated xylene at 181 nl/hr. The tolualdehyde content of the xylenes before and after contact with air are shown in TABLE I.

TABLE I

| | FORMATION OF TOLUALDEHYDE IN XYLENE | | | |
|---|---|---|---|---|
| Xylene Type | Initial Aldehyde Conc. ppm. | History of Heating | | Final Aldehyde Concentration, ppm |
| | | Temp., °C. | Time, hr | Aerated | |
| ortho | 14 | 60 | 72 | No | 70 |
| ortho | 19 | 60 | 89.5 | No | 46 |
| ortho | 44 | 60 | 45 | Yes | 67 |
| ortho | 23 | 60 | 48 | No | 540 |
| ortho | 23 | 60 | 48 | Yes | 750 |
| ortho | 540 | 60 | 264 | No | 685 |
| ortho | 750 | 60 | 264 | Yes | 944 |

TABLE I-continued

FORMATION OF TOLUALDEHYDE IN XYLENE

| Xylene Type | Initial Aldehyde Conc. ppm. | History of Heating | | | Final Aldehyde Concentration, ppm |
|---|---|---|---|---|---|
| | | Temp., °C. | Time, hr | Aerated | |
| para | 308 | 60 | 72 | No | 419 |

The data in TABLE II will illustrate the benefits of the present inventive concept for suppressing the formation of tolualdehyde in xylene.

TABLE II

SUPPRESSION OF TOLUALDEHYDE FORMATION IN ORTHO-XYLENE

| Initial Aldehyde, ppm | History of Heating | | | | Final Aldehyde Concentration ppm |
|---|---|---|---|---|---|
| | Temp., °C. | Time, hr | Additive, | ppm | Aerated 181 nl/hr |
| 15 | 60 | 72 | di(c16) ester | 100 | No | 49 |
| 19 | 60 | 89.5 | di(c16) ester | 1000 | No | 21 |

TABLE II-continued

SUPPRESSION OF TOLULALDEHYDE FORMATION IN ORTHO-XYLENE

| Initial Aldehyde, ppm | History of Heating | | | | Final Aldehyde Concentration ppm |
|---|---|---|---|---|---|
| | Temp., °C. | Time, hr | Additive, | ppm | Aerated 181 nl/hr |
| 19 | 60 | 89.5 | di(c16) ester | 500 | No | 21 |
| 19 | 60 | 45 | di(c16) ester | 1000 | Yes | 34 |
| 17 | 60 | 45 | di(c16) ester | 500 | Yes | 32 |
| 373 | 60 | 92 | di(c16) ester | 1000 | Yes | 341 |

The invention claimed is:

1. A method of suppressing tolualdehyde formation in a xylene contacted with air which comprises dissolving in the xylene thiodipropionic acid or a di($C_1$ to $C_{20}$ alkyl) ester thereof in an amount of upward from 100 ppm of the free acid or a chemically equivalent amount of the diester.

2. The method of claim 1 wherein the dialkyl ester is a di($C_6$ to $C_{18}$ alkyl) ester of thiodipropionic acid.

3. The method of claim 2 wherein said diester is added to the xylene in an amount chemically equivalent to from 140 up to 280 ppm of thiodipropionic acid.

4. The method of claim 3 wherein o-tolulaldehyde formation is suppressed by the addition of dilauryl thiodipropionate thereto in an amount of from 500 to 1000 ppm based on o-xylene.

* * * * *